United States Patent [19]

Suyama et al.

[11] Patent Number: 5,674,740
[45] Date of Patent: Oct. 7, 1997

[54] ENZYMATIC DECOMPOSITION OF POLYCARBONATE RESIN

[75] Inventors: Tetsushi Suyama, Tsukuba; Yutaka Tokiwa, Tsuchiura, both of Japan

[73] Assignee: Director-General of Agency of Industrial Science and Technology, Japan

[21] Appl. No.: 559,573

[22] Filed: Nov. 16, 1995

[30] Foreign Application Priority Data

Nov. 28, 1994 [JP] Japan .................................. 6-292658

[51] Int. Cl.⁶ .................................................. D06M 16/00
[52] U.S. Cl. ........................ 435/264; 435/262; 435/262.5
[58] Field of Search .................................. 435/252, 264, 435/262.5

[56] References Cited

PUBLICATIONS

Tokiwa et al. "Purification and Some Properties of Poly Ethylene Adipate Degrading Enzyme by Penicillium Sp." 1977, Abstract.

*Primary Examiner*—Lien Tran
*Attorney, Agent, or Firm*—Lorusso & Loud

[57] ABSTRACT

A polycarbonate resin, such as a poly(tetramethylene carbonate) resin, is enzymatically decomposed by contacting the polycarbonate resin with at least one enzyme selected from porcine pancreas lipase, Pseudomonas sp. lipase and Pseudomonas sp. lipoprotein lipase in the presence of water.

3 Claims, No Drawings

ENZYMATIC DECOMPOSITION OF POLYCARBONATE RESIN

BACKGROUND OF THE INVENTION

This invention relates to a method of decomposing a polycarbonate resin.

Polycarbonate resins which are produced using carbon dioxide as a raw material and which are biodegradable are now drawn much attention as a substitute for conventional plastics. In particular, poly(tetramethylene carbonate) which can be produced on an industrial scale at relative low costs is expected to be widely utilized in future.

It is known that an aliphatic polycarbonate is biodegradable. Thus, there is a report disclosing that an aliphatic polycarbonate placed in the abdomen of a rabbit spontaneously disappeared. It is also reported that an aliphatic polycarbonate dispersed in an agar culture medium was decomposed upon growth of a microorganism in the culture medium.

JP-B-54-44749 and JP-B-57-9354 disclose a method of decomposing a polyester by treatment with lipase. The polyesters specifically disclosed in the working examples are poly(ethylene adipate), polycaprolactone, poly(ethylene phthalate) and polymethylone terephthalate).

SUMMARY OF THE INVENTION

It is an object of the present invention to provide a method which can enzymatically effectively decompose polycarbonate resins.

In accomplishing the above object, there is provided in accordance with the present invention a method of decomposing a polycarbonate resin, comprising contacting said polycarbonate resin with at least one enzyme selected from the group consisting of porcine pancreas lipase, Pseudomonas sp. lipase and Pseudomonas liporotein lipase in the presence of water.

Other objects, features and advantages of the present invention will become apparent from the detailed description of the preferred embodiments to follow.

DETAILED DESCRIPTION OF THE PREFERRED EMBODIMENTS OF THE INVENTION

The polycarbonate resin to be used in the present invention is a resin such as a homopolymer, a copolymers and a modified polymer thereof, having carbonic ester linkages —O—R—O—CO— as major components. An aliphatic polycarbonate resin, such as poly(ethylene carbonate), poly(propylene carbonate), poly(tetramethylene carbonate), poly(cyclohexene carbonate), a copolymer thereof, a modified product thereof or a mixture thereof, is especially preferably used. The polycarbonate resin may be used as a mixture with another synthetic or natural polymer such as polyethylene, polystyrene or starch and/or with an inorganic material such as calcium carbonate.

The polycarbonate resin is contacted with at least one enzyme selected from porcine pancreas lipase, Pseudomonas sp. lipase and Pseudomonas liporotein lipase in the presence of water. These enzyme preparations may be coramercially available. For reasons of high decomposing activity, the use of porcine pancreas lipase is preferred.

The decomposition is preferably performed at a temperature of 0°–70° C. and a pH of 3–10, more preferably 20°–50° C. and a pH of 6–9.

The following examples will further illustrate the present invention.

EXAMPLE 1

Decomposition of Polycarbonate Using Porcine pancreas Lipase (A) Enzyme Activity on Olive Oil In an L-shaped test tube were charged 2.0 g of olive oil and 10 ml of 20 mM phosphate-potassium buffer (pH: 7.0) and the mixture was subjected to pre-incubation by shaking at 35° C. for 30 minutes at a rate of 120 r.p.m. (revolutions per minute). Thereafter, a solution containing 6.7 mg of porcine pancreas lipase (Type VI-S available from Sigma Chemical Inc.) was added to the pre-incubated solution and the mixture was reacted for 30 minutes under the same conditions as those in the pre-incubation. The reaction was terminated by addition of 40 ml of ethanol. The reaction mixture was then measured for the amount of free acid by titration with 0.05N aqueous sodium hydroxide. The above procedure was repeated in the same manner as described except that no lipase was used (control). The enzyme activity of the porcine pancreas lipase on the olive oil was determined based on the results of the above measurements.

(B) Enzyme Activity on Polycarbonate

In a cylindrical vial were charged 0.1 g of poly (tetramethylene carbonate) having a number average molecular weight of 2,000 and a particle size of 180–300 μm, 25 ml of 50 mM phosphate-potassiumbuffer (pH: 7.0), sodium azide (0.1% by weight) and a surfactant (PLYSURF (trademark), 50 ppm by weight) and the mixture was subjected to pre-incubation by shaking at 35° C. overnight at a rate of 180 r.p.m. The pre-incubated mixture was then mixed with a solution of the above enzyme (enzyme content: 6.3 mg) and supernatant (5 ml) was immediately sampled. The sample was filtered with a Millipore filter (0.45 μm) and the filtrate was measured for the initial value ($T_{ini}$) of the total organic carbon content (TOC). The remainder of the enzyme-containing mixture (about 20 ml) was reacted at 35° C. for 18 hours with shaking at 180 r.p.m. Thereafter, the supernatant was sampled and measured for TOC ($T_{18}$). The above procedure was repeated in the same manner as described except that no enzyme was added (control). The TOC values ($TC_{ini}$ and $TC_{18}$) for the control sample were then measured. The actual TOC ($T_{abs}$) was then calculated according to the following equation:

$$T_{abs}=T_{18}-T_{ini}-(TC_{18}-TC_{ini})$$

The enzyme activity $T_{abs}$ of the porcine pancreas lipase on the polycarbonate is converted into an activity (μg TOC/hour) per 100 μmol/minute of the olive oil decomposition activity of the porcine pancreas lipase. The result is shown in Table 1.

EXAMPLE 2

Decomposition of Polycarbonate Using Pseudomonas sp. Lipase

Example 1 was repeated in the same manner as described except that 0.12 mg of Pseudomonas sp. lipase (Type XIII, commercially available from Sigma Chemical Inc.) was used as an enzyme in the determination of the olive oil decomposition activity and 0.78 mg of the same Pseudomonas sp. lipase was used as an enzyme in the determination of the polycarbonate decomposition activity. The results are summarized in Table 1.

EXAMPLE 3

Decomposition of Polycarbonate Using Pseudomonas sp. Lipoprotein Lipase

Example 1 was repeated in the same manner as described except that 0.1 mg of Pseudomonas sp. liporotein lipase (Type A, commercially available from TOYOBO Co., Ltd.) was used as an enzyme in the determination of the olive oil decomposition activity and 3.6 mg of the same Pseudomonas sp. lipoprotein lipase were used as an enzyme in the determination of the polycarbonate decomposition activity. The results are summarized in Table 1.

Comparative Example 1

Decomposition of Polycarbonate Using *Mucor javanicus* Lipase

Example 1 was repeated in the same manner as described except that 13 mg of *Mucor javanicus* lipase (Mucor Lipase M, commercially available from BIOCATALYSTS Ltd.) were used as an enzyme in the determination of the olive oil decomposition activity and 200 mg of the same *Mucor javanicus* lipase were used as an enzyme in the determination of the polycarbonate decomposition activity. The results are summarized in Table 1.

Comparative Example 2

Decomposition of Polycarbonate Using *Penicillium roqueforti* Lipase

Example 1 was repeated in the same manner as described except that 50 mg of *Penicillium roqueforti* lipase (Penicillin Lipase R, commercially available from BIOCATALYSTS Ltd.) was used as an enzyme in the determination of the olive oil decomposition activity and 240 mg of the same *Penicillium roqueforti* lipase were used as an enzyme in the determination of the polycarbonate decomposition activity. The results are summarized in Table 1.

Comparative Example 3

Decomposition of Polycarbonate Using *Phycomyces nitens* Lipase

Example 1 was repeated in the same manner as described except that 0.07 mg of *Phycomyces nitens* lipase (Lipase PN, commercially available from Wako Pure Chemical Industries, Ltd.) was used as an enzyme in the determination of the olive oil decomposition activity and 12 mg of the same *Phycomyces nitens* lipase were used as an enzyme in the determination of the polycarbonate decomposition activity. The results are summarized in Table 1.

Comparative Example 4

Decomposition of Polycarbonate Using *Rhizopus delemer* Lipase

Example 1 was repeated in the same manner as described except that 0.07 mg of *Rhizopus delemer* lipase (commercially available from Seikagaku Corporation) was used as an enzyme in the determination of the olive oil decomposition activity and 0.98 mg of the same *Rhizopus delemer* lipase was used as an enzyme in the determination of the polycarbonate decomposition activity. The results are summarized in Table 1.

Comparative Example 5

Decomposition of Polycarbonate Using *Rhizopus arrhizus* Lipase

Example 1 was repeated in the same manner as described except that 0.0018 mg (5 µl of 100-fold diluted solution of the liquid product) of *Rhizopus arrhizus* lipase (commercially available from Boehringer Mannheim GmbH) was used as an enzyme in the determination of the olive oil decomposition activity and 0.49 mg (140 µl of the 100-fold diluted solution) of the same *Rhizopus arrhizus* lipase was used as an enzyme in the determination of the polycarbonate decomposition activity. The results are summarized in Table 1.

Comparative Example 6

Decomposition of Polycarbonate Using *Rhizopus arrhizus* Lipase

Example 1 was repeated in the same manner as described except that 0.3 mg (5 µl of 15-fold diluted solution of the liquid product) of *Rhizopus arrhizus* lipase (Type XI coraraercially available from Sigma Chemical Inc.) was used as an enzyme in the determination of the olive oil decomposition activity and 58 mg (290 µl of the 5-fold diluted solution) of the same *Rhizopus arrhizus* lipase were used as an enzyme in the determination of the polycarbonate decomposition activity. The results are summarized in Table 1.

Comparative Example 7

Decomposition of Polycarbonate Using *Chromobacterium viscosum* Lipase

Example 1 was repeated in the same manner as described except that 0.05 mg of *Chromobacterium viscosum* lipase (Chromobacteria Lipase V, commercially available from BIOCATALYSTS Ltd.) was used as an enzyme in the determination of the olive oil decomposition activity and 15 mg of the same *Chromobacterium viscosum* lipase was used as an enzyme in the determination of the polycarbonate decomposition activity. The results are summarized in Table 1.

Comparative Example 8

Decomposition of Polycarbonate Using *Chromobacterium viscosum* Lipase

Example 1 was repeated in the same manner as described except that 0.004 mg of *Chromobacterium viscosum* lipase (Type XII, commercially available from Sigma Chemical Inc.) was used as an enzyme in the determination of the olive oil decomposition activity and 0.91 mg of the same *Chromobacterium viscosum* lipase was used as an enzyme in the determination of the polycarbonate decomposition activity. The results are summarized in Table 1.

Comparative Example 9

Decomposition of Polycarbonate Using *Candida cylindacea* Lipase

Example 1 was repeated in the same manner as described except that 0.05 mg of *Candida cylindacea* lipase (Type VII-S, commercially available from Sigma Chemical Inc.) was used as an enzyme in the determination of the olive oil decomposition activity and 6.0 mg of the same *Candida cylindacea* lipase was used as an enzyme in the determination of the polycarbonate decomposition activity. The results are summarized in Table 1.

Comparative Example 10

Decomposition of Polycarbonate Using *Candida cylindacea* Lipase

Example 1 was repeated in the same manner as described except that 0.002 mg of *Candida cylindacea* lipase (commercially available from Boehringer Mannheim GmbH) was used as an enzyme in the determination of the olive oil decomposition activity and 0.68 mg of the same *Candida cylindacea* lipase was used as an enzyme in the determination of the polycarbonate decomposition activity. The results are summarized in Table 1.

Comparative Example 11

Decomposition of Polycarbonate Using *Candida cylindacea* Lipase

Example 1 was repeated in the same manner as described except that 0.02 mg of *Candida cylindacea* lipase (Candida Lipase B, commercially available from BIOCATALYSTS Ltd.) was used as an enzyme in the determination of the olive oil decomposition activity and 3.2 mg of the same *Candida cylindacea* lipase were used as an enzyme in the determination of the polycarbonate decomposition activity. The results are summarized in Table 1.

Comparative Example 12

Decomposition of Polycarbonate Using *Candida cylindacea* Cholesterol Esterase Example 1 was repeated in the same manner as described except that 0.008 mg of *Candida cylindacea* cholesterol esterase (commercially available from Seikagaku Corporation) was used as an enzyme in the determination of the olive oil decomposition activity and 0.57 mg of the same *Candida cylindacea* cholesterol esterase was used as an enzyme in the determination of the polycarbonate decomposition activity. The results are summarized in Table 1.

TABLE 1

| Example No. | Comparative Example No. | Poly(tetramethylene carbonate) Decomposition Activity TOC (µg/hour)* |
|---|---|---|
| 1 | | 460 |
| 2 | | 290 |
| 3 | | 130 |
| | 1 | not detected |
| | 2 | not detected |
| | 3 | not detected |

TABLE 1-continued

| Example No. | Comparative Example No. | Poly(tetramethylene carbonate) Decomposition Activity TOC (µg/hour)* |
|---|---|---|
| | 4 | not detected |
| | 5 | 1 |
| | 6 | 2 |
| | 7 | 3 |
| | 8 | 5 |
| | 9 | 6 |
| | 10 | 10 |
| | 11 | 37 |
| | 12 | 9 |

*per 100 µmol/minute of the olive oil decomposition activities

In Table 1, the activity of each of the enzymes in the decomposition of poly(tetramethylene carbonate) is expressed in terms of TOC (µg/hour) obtained by using an amount of the enzyme that gives the predetermined olive oil decomposing activity of 100 µmol/minute. The results shown in Table 1 indicate that the polycarbonate decomposition activity greatly varies with the derivation thereof. Among a large number of lipase preparations, only porcine pancreas lipase, Pseudomonas sp. lipase and Pseudomonas sp. liporotein lipase exhibit high activity. Rhizopus lipase which is known to show a high decomposition activity to polyesters such as poly(ethylene adipate) and polycaprolactone has little activity to poly(tetramethylene carbonate).

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method of decomposing an aliphatic polycarbonate resin, comprising contacting said aliphatic polycarbonate resin with at least one enzyme selected from the group consisting of porcine pancreas lipase, Pseudomonas sp. lipase and Pseudomonas sp. lipoprotein lipase in the presence of water, wherein said polycarbonate resin is a tetramethylene group-containing polycarbonate selected from the group consisting of polycarbonate homopolymers, polycarbonate copolymers and modified polycarbonates containing carbonic ester linkages —O—R—O—CO— as a major component, wherein R is a tetramethylene group.

2. A method as claimed in claim 1, wherein said aliphatic polycarbonate resin is a poly(tetramethylene carbonate) resin.

3. A method as claimed in claim 1, wherein said contacting of said aliphatic polycarbonate with at least one enzyme is performed at a temperature of 20°–50° C. and a pH of 6–9.

* * * * *

UNITED STATES PATENT AND TRADEMARK OFFICE
CERTIFICATE OF CORRECTION

PATENT NO. : 5,674,740
DATED : October 7, 1997
INVENTOR(S) : SUYAMA et al

It is certified that error appears in the above-indentified patent and that said Letters Patent is hereby corrected as shown below:

Col. 1, line 25, "polymethylone" should read --poly(ethlene--.

Col. 2, line 31, "potassiumbuffer" should read --potassium-buffer--.

Col. 4, line 27, "corarercially" should read --commercially--.

Signed and Sealed this

Twenty-ninth Day of September, 1998

Attest:

BRUCE LEHMAN

Attesting Officer

Commissioner of Patents and Trademarks